(12) United States Patent
Colvin, Jr.

(10) Patent No.: US 10,662,333 B2
(45) Date of Patent: May 26, 2020

(54) NIR LONG LIFETIME INDICATOR MOLECULE

(71) Applicant: Arthur E. Colvin, Jr., Mount Airy, MD (US)

(72) Inventor: Arthur E. Colvin, Jr., Mount Airy, MD (US)

(73) Assignee: Profusa, Inc., Emeryville, CA (US)

( * ) Notice: Subject to any disclaimer, the term of this patent is extended or adjusted under 35 U.S.C. 154(b) by 0 days.

(21) Appl. No.: 16/308,675

(22) PCT Filed: Jun. 16, 2017

(86) PCT No.: PCT/US2017/037890
§ 371 (c)(1),
(2) Date: Dec. 10, 2018

(87) PCT Pub. No.: WO2017/218903
PCT Pub. Date: Dec. 21, 2017

(65) Prior Publication Data
US 2019/0352510 A1    Nov. 21, 2019

Related U.S. Application Data

(60) Provisional application No. 62/351,736, filed on Jun. 17, 2016.

(51) Int. Cl.
| C09B 62/84 | (2006.01) |
| A61K 49/00 | (2006.01) |
| G01N 33/58 | (2006.01) |
| G01N 33/66 | (2006.01) |
| C09B 69/10 | (2006.01) |

(52) U.S. Cl.
CPC .......... *C09B 62/84* (2013.01); *A61K 49/0036* (2013.01); *C09B 69/10* (2013.01); *G01N 33/582* (2013.01); *G01N 33/66* (2013.01)

(58) Field of Classification Search
None
See application file for complete search history.

(56) References Cited

U.S. PATENT DOCUMENTS

| 2012/0168697 A1 | 7/2012 | Thompson et al. |
| 2014/0088383 A1 | 3/2014 | Colvin et al. |
| 2014/0148596 A1 | 5/2014 | Dichtel et al. |
| 2014/0286875 A1 | 9/2014 | Gamsey et al. |

FOREIGN PATENT DOCUMENTS

WO    WO 2017/218903 A1    12/2017

OTHER PUBLICATIONS

Wang et al journal of food and drug analysis 23 (2015) 191-200.*
International Search Report and Written Opinion dated Sep. 11, 2017, for International Application No. PCT/US2017/037890, 5 pages.
Klonoff, "Overview of Fluorescence Glucose Sensing: A Technology with a Bright Future," Journal of Diabetes Science and Technology, vol. 6, Issue 6, Nov. 2012.
Quaranta et al., "Indicators for optical oxygen sensors," Bioanal Rev. Dec. 2012; 4(2-4): 115-157.

* cited by examiner

*Primary Examiner* — Kamal A Saeed
(74) *Attorney, Agent, or Firm* — Cooley LLP

(57) ABSTRACT

The invention relates to a porphyrin time domain indicator. The indicator may be used for detection of a particular analyte in vivo or in vitro. The indicator may be used for detection of glucose in vivo or in vitro.

16 Claims, No Drawings

NIR LONG LIFETIME INDICATOR MOLECULE

CROSS-REFERENCE TO RELATED APPLICATION

This application is a U.S. National Stage of PCT Application No. PCT/US2017/037890, filed Jun. 16, 2017, which claims the benefit of priority to U.S. Provisional Application No. 62/351,736, filed Jun. 17, 2016, each of which is incorporated herein by reference in their entirety.

FIELD OF THE INVENTION

The invention relates to a porphyrin time domain indicator. The indicator may be used for detection of a particular analyte in vivo or in vitro. The indicator may be used for detection of glucose in vivo or in vitro.

TECHNICAL BACKGROUND

Diagnosis, treatment and management of some medical conditions require monitoring of the presence or concentration of an analyte in the afflicted organ or tissue. Current monitoring methods are expensive, cumbersome, time consuming, and do not provide accurate, continuous information. Thus, there is clearly a need for a better long-term tissue monitoring system. Preferably analyte concentration should be measured non-invasively or minimally-invasively with minimal user maintenance Furthermore, sensors should preferably last for days to months.

Such real-time, continuous measurement of analyte presence or concentration in tissues can be achieved by the use of sensors inserted or implanted into the tissue and measuring the signal generated by the sensor by a device located outside the body. Oxygen sensors are described in U.S. Patent Publication No. 2014/0286875, which is hereby incorporated herein by its entirety. There is a need for stable, near-IR luminescent compounds and sensors for direct, rapid and accurate measurement of analyte levels in tissue, including tissues in vivo. In addition, there is a need for stable, near-IR luminescent compounds and sensors for direct, rapid and accurate measurement of analyte levels in tissue, including tissues in vivo.

SUMMARY

Some embodiments described herein relates to a compound having the following structure:

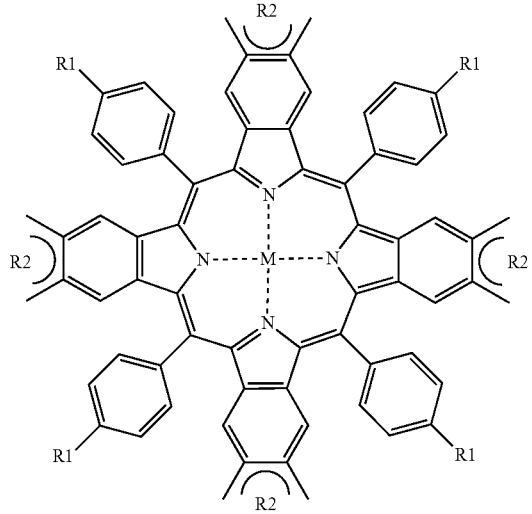

wherein

M is a metal which forms a chelated luminescent complex with tetraphenyl porphyrin ligand base structure or derivatives thereof; R1 may be a linker, a polymerizable group, or H;

at least one R2 comprises a recognition element capable of reversible or irreversible chemical binding to an analyte, or specifically interacting with or detecting an analyte.

In an certain embodiment, M may be selected from the group consisting of: Pt, Pd, Al, Ru, Os, Ir, Al, Cu, Ag, Pb, Au, Eu, Tb, Rh, and Ni In an embodiment, R1 may be selected from the group consisting of: vinyl, acrylate, methacrylate, amides, polyethylene glycols, and methacrylamides, or carboxy, amine, sulfhydryl, or sulfonate. In an embodiment, the R1 may include:

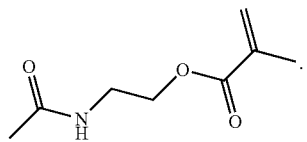

In an aspect of the embodiment, a polymeric backbone structure may be covalently bonded to R1. The polymeric backbone structure may be a polymer, or copolymer, including a hydrogel or a derivative thereof.

In an embodiment, the recognition element may be a boronate or derivative thereof. In an aspect of the embodiment, the recognition element may be selected from the group consisting of: boronate coupled into a phenyl, napthyl, anthryl; mono boronates of phenyl boronate, napthyl boronate, anthryl boronate; and bis-boronate derivations of phenyl, napthyl, or anthryl groups.

In an embodiment, R2 may be independently selected from the group consisting of:

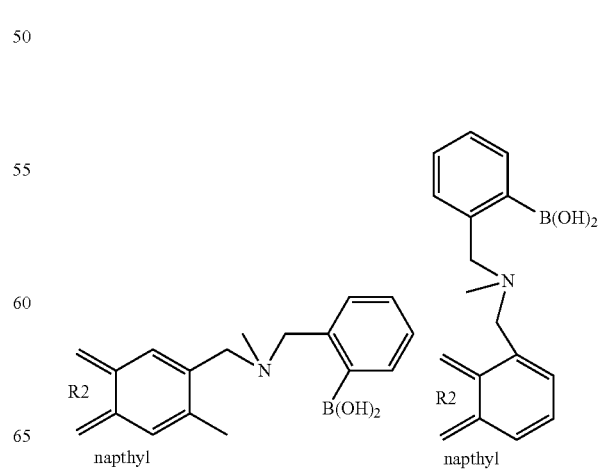

napthyl        napthyl

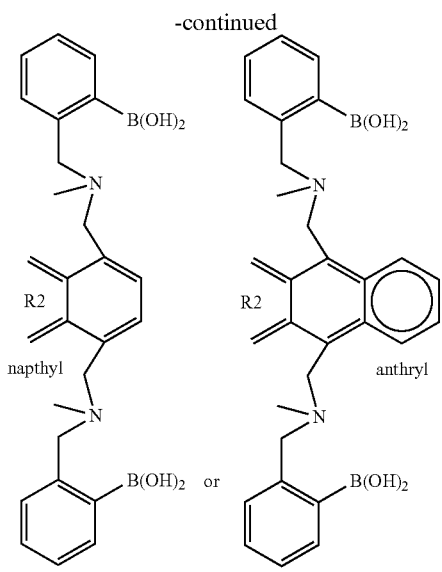

In an embodiment, the detected analyte is selected from the group consisting of glucose. In an embodiment, the detected analyte is glucose

DETAILED DESCRIPTION

Some embodiments described herein relate to a NIR lifetime modulated indicator molecule system configured for glucose as an example operating in the double and triple digit microsecond decay time range. Long lifetime indicators have substantial value for commercial sensors, enabling products of low cost, small size, very long useful lifetime, high accuracy, and stable calibration. As an example, long lifetime indicators would be very valuable as in vivo glucose sensors.

Compounds described herein have the desirable properties of NIR wavelength excitation and emission, long lifetime, water solubility, and stable calibration. In addition, these compounds include a recognition element that confers the ability to detect a particular analyte, such as glucose. The analyte to be detected is dependent on the particular recognition element and configuration within the molecular structure of the overall indicator.

In an embodiment, the indicators described herein may be used for in vivo detection of glucose, for example, in a human or an animal. In a further embodiment, the indicators may be used for in vitro detection of glucose, for example, food and beverage formulation and processing, brewing and wine making, grain derived distillation production, baker's yeast production, energy applications such as ethanol for fuel and biofuel formulation and processing, industrial and medical glucose processing and supply, industrial biotech including fermentation and bioprocessing, pharmaceuticals such as antibiotics, proteins, etc. cell culture, and drug formulation, agricultural monitoring such as soybeans, fruits, and vegetable products.

Recognition Elements

The compounds described herein include a recognition element structure in addition to the core porphyrin structure. Upon chemical interaction of the recognition element structure with an analyte, resulting in an induced change within the core porphyrin structure, the decay time of the luminescent emission from the metalloporphyrin is altered in proportion to the presence and concentration of the analyte.

A recognition element of the compound confers the ability to detect a particular analyte. In an embodiment, the recognition element structure may include a chemical moiety which reversibly binds or electrostatically interacts with an analyte in such as way as to cause a perturbance in resonant electron structure within the overall indicator molecule resulting in a change in luminescence lifetime. In an embodiment, the recognition element may be a chemical moiety. In an example embodiment configured for glucose recognition, the moiety may be boronic acid, boronate, or boronic acid derivatives such as bis-boronates. In an embodiment, the compound can include 1, 2, 3, or 4 recognition elements.

Analyte

Described herein are luminescent indicator compounds useful, for example, in sensing and imaging applications. For example, the compounds described herein provide accurate and long term measurements of an analyte in vivo and in vitro. In an embodiment, the analyte may be glucose. Further, described herein are polymers including the luminescent indicator compounds described herein.

Additionally, described herein are sensors including the compounds and/or polymers described herein. The sensors may be implanted into a tissue of a subject and used for long-term or short-term continuous and semi-continuous collection of data of various biochemical analytes, optionally without the use of implantable hardware of any type. In one aspect, the sensors are tissue integrating, e.g., allow capillaries to grow in close proximity to all regions of the sensor (e.g., on the surface and inside), which results in accurate analyte measurements, including over long term.

Advantages of the compounds and polymers provided herein include, but are not limited to: (1) excitation and emission wavelengths in the optical window of the skin (approximately 550 nm to 1000 nm) allowing detection of analytes deep within a tissue or an organ; (2) high signal-to-noise ratio; (3) large Stokes shifts and emission; (4) photostablity, e.g., the dyes and/or polymers do not undergo rapid photobleaching Advantages of the sensors described herein include, but are not limited to: providing devices that generate stable signal over a long period of time (e.g., greater than a week, greater than a month, greater than 6 months), (2) providing devices that are placed or implanted and integrate into the subject's tissue (e.g., through tissue and/or capillary ingrowth); (3) providing devices which can be implanted through syringe injection or trocar injection, meaning that no surgery is required to put the sensing media in place in the body; (4) providing devices that do not include sensor electronics in the body; (5) providing devices that accurately assess analyte concentration for long periods of time (e.g., greater than a week, typically weeks, months or years) and/or (6) providing devices of small dimensions which will give result in increased patient comfort and better acceptance by the body.

It must be noted that, as used in this specification and the appended claims, the singular forms "a", "an", and "the" include plural referents unless the content clearly dictates otherwise. Thus, for example, reference to a sensor comprising "a sensing moiety" includes devices comprising of two or more sensing moieties. Likewise, reference to "an analyte" refers to two or more analytes. Some embodiments are described herein as "tissue integrating," which can refer to a material (e.g., scaffold) which, when integrated into living tissue remains in close proximity with the blood vessels of the tissue (e.g., capillaries).

Some embodiments are described herein as being "long-term," which can mean that the implant senses the analyte for greater than about 7 days, for example weeks, months, or years.

Luminescent NIR Dyes

Certain embodiments described herein relates to a compound of Formula I having the following structure:

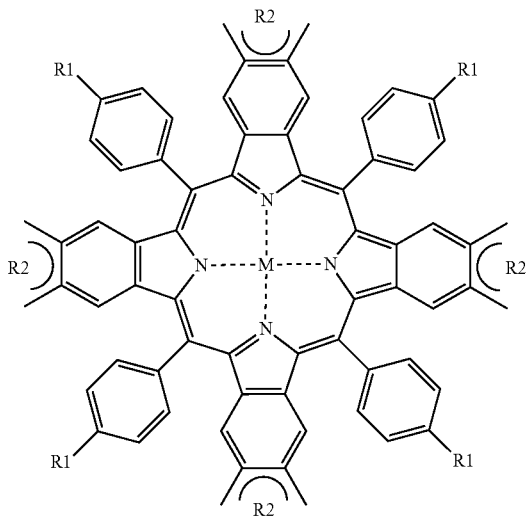

(Formula I)

wherein
M is a metal which forms a chelated luminescent complex with tetraphenyl porphyrin ligand base structure or derivatives thereof;
R1 is a linker, a polymerizable group, or H;
at least one R2 comprises a recognition element capable of reversible or irreversible chemical binding to an analyte, or specifically interacting with or detecting an analyte.

In an embodiment, M may be selected from the group consisting of: Pt, Pd, Al, Ru, Os, Ir, Al, Cu, Ag, Pb, Au, Eu, Tb, Rh, and Ni.

In a particular embodiment, R2 is a linker or H.

In a further embodiment, R1 may be independently selected from the group consisting of: vinyl, acrylate, methacrylate, amides, polyethylene glycols, methacrylamides, carboxy, amine, sulfhydryl, and sulfonate.

In yet a further embodiment R1 may be independently selected from the group consisting of: vinyl, acrylate, methacrylate, amides, polyethylene glycols, and methacrylamides.

In a still further embodiment, R1 may be:

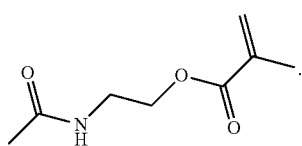

In a particular embodiment, R1 is the same.

In an aspect of the embodiment, a polymeric backbone structure may be covalently bonded to R1. The polymeric backbone structure may be a polymer, or copolymer, including a hydrogel or a derivative thereof.

In another embodiment, the recognition element may independently be a boronate or derivative thereof. In an aspect of the embodiment, the recognition element may independently be selected from the group consisting of: boronate coupled into a phenyl, napthyl, or anthryl; mono boronates of phenyl boronate, napthyl boronate, anthryl boronate; and bis-boronate derivations of phenyl, napthyl, or anthryl groups.

In an embodiment, R2 may be independently selected from the group consisting of:

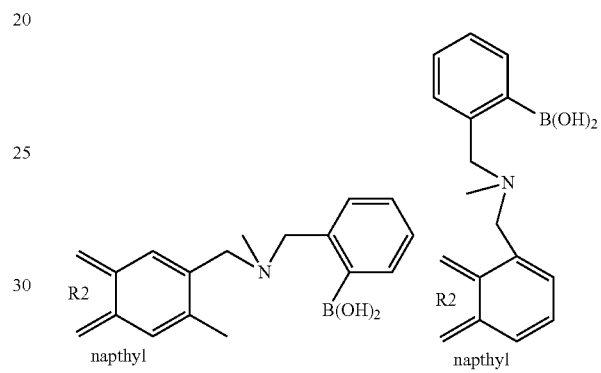

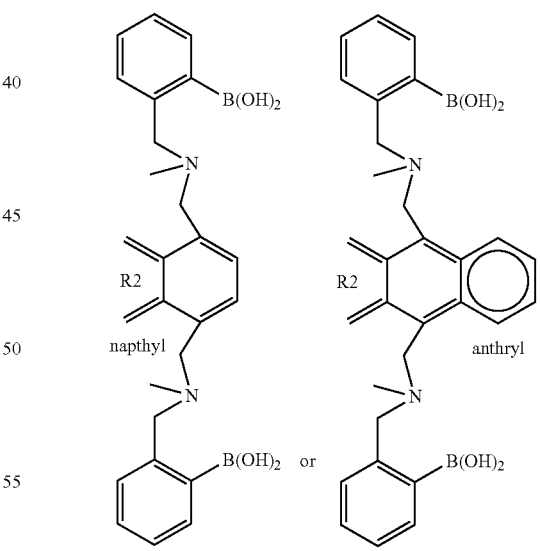

In an embodiment, the detected analyte is selected from the group consisting of glucose. In an embodiment, the detected analyte is glucose.

Some embodiments described herein relate to a compound of Formula I:

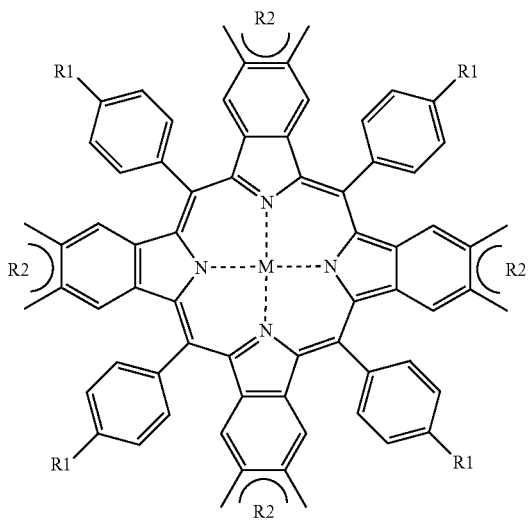

wherein M can be any metal which can form a chelated luminescent complex with tetraphenyl porphyrin ligand base structure or derivatives thereof which may include Pt, Pd, Al, Ru, Os, Ir, Al, Cu, Ag, Pb, Au, Eu, Tb, Rh, Ni or others.

Each R1 may independently include between zero and four polymerizable or dendritic extension derivation group or linker groups such as:

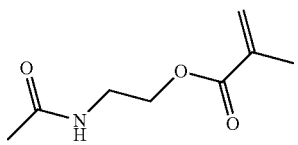

or may include vinyl, acrylate, methacrylate, amides, polyethylene glycols, methacrylamides, carboxy, amine, sulfhydryl, sulfonate and/or other groups capable of covalent linkage or by copolymerization or post polymerization covalent reaction into or onto a polymeric backbone structure for immobilization of the metalloporphyrin. R1 may include the same or different groups of the following types. In the simplest configuration, R1 may include —H in one through four positions. R1 may also include groups to adjust the solubility of the molecule within its intended environment (solvent) of use such as halogen, hydroxyl, carboxy, sulfonate or combinations of or derivatives thereof. R1 may also include zero through four linker groups for subsequent immobilization to a solid substrate in one example such a —SH for immobilization to gold substrates or nanoparticles, or —NH2 for immobilization to an organic or biochemical substrate through for example a gluteraldehyde reaction, or in others. R1 may also be between one and four polymerizable monomeric functional groups such as acrylimide, acrylate, methacrylate or others. In all cases R1 may be occupied in between zero and all four positions.

R2 can be an independent individual group or between 1-4 of the same groups which group or groups may include a recognition element capable of binding to glucose such as boronate coupled into a phenyl, napthyl, anthryl and/or mono boronates of phenyl boronate, napthyl boronate, anthryl boronate, or bis-boronate derivations of phenyl, napthyl, or anthryl groups such as:

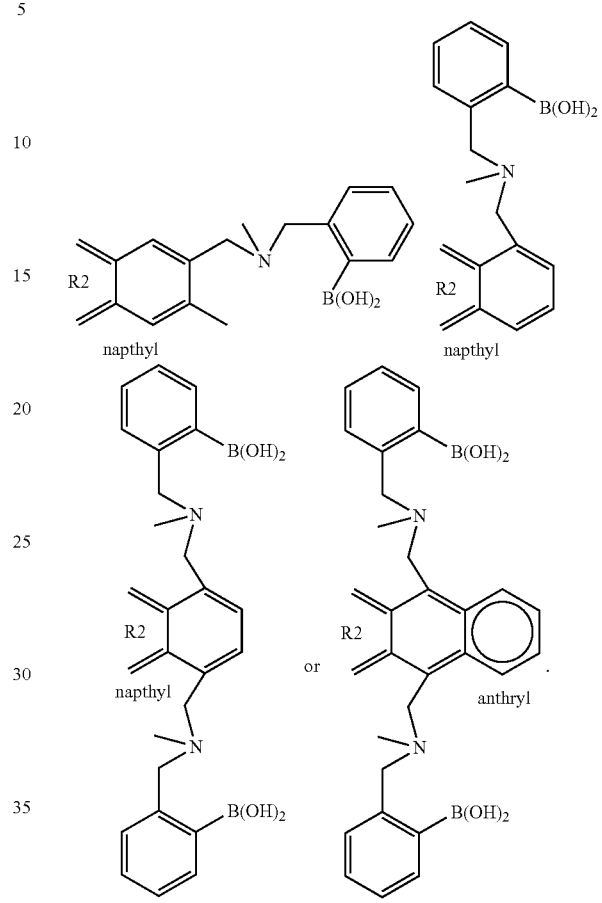

In an embodiment, each R1 may independently include between zero and four polymerizable or dendritic extension derivation group or linker groups such as:

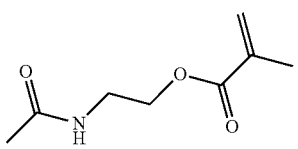

In a further embodiment each R1 may independently include vinyl, acrylate, methacrylate, amides, polyethylene glycols, methacrylamides, carboxy, amine, sulfhydryl, sulfonate and/or other groups capable of covalent linkage or by copolymerization or post polymerization covalent reaction into or onto a polymeric backbone structure for immobilization of the metalloporphyrin.

In a yet further embodiment each R1 may independently include vinyl, acrylate, methacrylate, amides, polyethylene glycols, methacrylamides, and/or other groups capable of covalent linkage or by copolymerization or post polymerization covalent reaction into or onto a polymeric backbone structure for immobilization of the metalloporphyrin.

In a still further embodiment each R1 may include vinyl, acrylate, methacrylate, amides, polyethylene glycols, methacrylamides.

In an embodiment, at least one of the R2 groups includes a recognition element. In an embodiment, 1, 2, 3, or 4 of the R2 groups includes a recognition element. In an embodiment, 1, 2, or 3 of the R2 groups does not include a recognition element. For example, one R2 group may include napthyl boronate, and the three remaining R2 groups may include napthyl.

In an embodiment, the compound of Formula 1 is a near-IR luminescent dye. In an embodiment, the compound of Formula 1 has an emission maximum between 650 and 900 nm. In an embodiment, the compound of Formula 1 has an absorption maximum between 500 nm and 800 nm. The compound of Formula 1 may have an absorption maximum between 500 nm and 700 nm. In one embodiment, the compound of Formula 1 has an emission maximum between 500 and 1000 nm. In one embodiment, the compound of Formula 1 has an emission maximum between 650 and 900 nm. In an embodiment, the compound of Formula 1 has an emission maximum between 800 and 900 nm. In an embodiment, the compound of Formula 1 has an emission maximum between 760 and 860 nm. In one embodiment, the compound of Formula 1 of the present invention is photostable and has excitation and emission spectra in the NIR optical window of the skin.

Glucose Sensor

Glucose chemical indicators that are capable of serving as front end components within a signal transduction system are useful in the development of chemical and biochemical sensors which detect the presence and concentration of glucose. Such sensors are important in various applications such as industrial (industrial glucose, foods, brewing, energy), biotechnology (fermentation, cell culture, enzymology, others), as well as clinical and medical applications (diagnostics, diabetes, therapeutics).

Chemical glucose indicators of the type which can be useful within a general optical signal transduction scheme may be colorimetric, absorbance type, or luminescent (fluorescent or phosphorescent). Luminescent organic indicators are excited by a shorter higher energy wavelength of light from a light source, and in turn decay by emitting light at a longer, lower energy wavelength of light. The detection of the emitted light as either intensity or decay time (lifetime) can be correlated with analyte (glucose) concentration.

Fluorescence intensity measurement emitted light amplitude is correlated with concentration of the analyte. Intensity may be influenced by multiple other related or unrelated variables (other than the analyte) within the optical path that may decrease efficiency or induce errors on the system such as uncontrollable absorbance or scatter. Intensity measurements may also be influenced by indicator concentration changing due to leaching, thermal, or photo-degradation, excitation source drift, circuit drift, and others. Intensity measurements can be mitigated to a great extent by using ratiometric signal processing methods against a carefully crafted reference channel. However, it is also difficult, particularly within chemical and in-vivo applications, to achieve two completely identical channels in both hardware and chemistry in order the meet the requirement.

Luminescent lifetime is a measure of the time a fluorophore spends in the excited state before returning to the ground state by emitting a photon. The lifetimes of fluorophores can range from picoseconds to hundreds of nanoseconds. Low nanosecond time periods are typical. Phosphorescence lifetime, or emission from the triplet state of organic dyes, can range from microseconds to milliseconds. Tens and hundreds of microseconds are typical. Lifetime measurement methods, either fluorescent or phosphorescent, in one example, since they are unaffected by variable amplitude, have the advantage of minimizing the effect of photon scattering in thick or unknown layers of sampled tissues such as skin and be unaffected by unrelated and changing absorbance factors within the optical path of measurement, as described, for example in Klonoff, David C, Overview of Fluorescence Glucose Sensing: A Technology with a Bring Future, J. Diabetes Sci Technol. 2012 November; 6(6): 1242-1250, available at http://www.ncbi.nlm.nih.gov/pmc/articles/PMC3570863/, which is hereby incorporated by reference in its entirety.

Measurement of Lifetime (Time Domain or Frequency Domain Measurement)

The lifetime (decay time) is defined as the time required for an excited luminescent molecule to decay to 1/e of its excited state value. Lifetime can be measured either in time domain or in frequency domain. In time domain, the sample is excited with a pulse of light and then the time-dependent intensity is measured, and the decay time is calculated from the slope of the a plot of log l(t) versus t (slope=$-1/\tau$). In the frequency domain method, also known as phase modulation, the sample is excited with intensity-modulated light typically as a sine wave. The emission of the indicator is delayed in time relative to the excitation and the interval of the delay can be measured as a phase shift relative to the excitation waveform, which in turn can be used to calculate the decay time (lifetime) by well known deconvolution algorithms. The disclosure of Quaranta, Michela et al., Indicators for Optical Oxygen Sensors, Bioanal Rev. 2012 December; 4(2-4): 115-157, available at http://www.ncbi.nlm.nih.gov/pmc/articles/PMC3514702/ is hereby incorporated by reference in its entirety.

Lifetime measurement is generally advantageous over intensity measurement particularly within in-vivo applications in order to overcome uncontrollable intensity influential factors and imposed system errors unrelated to analyte concentration, such as tissue scatter, variable unrelated absorbance within the optical path, photo-bleaching, indicator degradation, and difficult tolerance geometric optical alignment for repeat measurements.

Long Lifetime versus Short Lifetime—chemistry and engineering compatibility advantages in product development and application.

A chemical sensor transduction system for commercial application is comprised of a chemical or biochemical front end that is analyte sensitive, typically termed an indicator, and often an opto-electronic signal capture and measurement system that is in turn sensitive to changes in the indicator and converts these changes into proportional and quantitative electrical signal as a signal transduction cascade. These different elements combine to form a transducer. A transducer is defined as a device that converts variations in a physical quantity, such as pressure or light brightness, into an electrical signal, or vice versa.

In the design of optical signal transducers using luminescent indicators, a very fast decay time requires very fast electronic circuitry in order to capture, convert into an electrical signal, and accurately measure that decay time. The circuitry to measure a fluorescent species decaying in nanoseconds must be much faster than a circuit needed to measure phosphorescent decay times typically in tens and hundreds of microseconds. Faster systems are much more expensive, larger, and require more power to operate. For commercial products based on lifetime measurement indicators, although both work well in chemistry, the engineering and hardware expense and complexity greatly favors long microsecond lifetimes in rendering an affordable and market suited commercial product. Therefore, a long lifetime indicator has particular commercial value in product development and marketability of sensor products.

For reasons described above, lifetime measurements provide multiple advantages over intensity measurements for in-vivo applications primarily related to signal capture fidelity, signal processing, cost, size, and accuracy of final measurement values. Also, calibration is much more stable for extended intervals of use with lifetime indicators since amplitude may deteriorate and lifetime accuracy remains the same, a particularly important factor for commercial product users. As mentioned above, fluorescent molecules decay in nanosecond time ranges, and phosphorescent molecules decay in microsecond to millisecond time ranges. All known luminescent glucose indicator molecules to date are fluorescent species and typically exhibit lifetimes of 14-20 nanoseconds. The invention herein is unique in teaching a long lifetime glucose indicator with decay times in microsecond range and most particularly in hundreds of microseconds.

The definition of decay time is the time it takes for the light emission from a fully excited species (lo) to decay down to a value equal to 1/e of lo). That is, the time it takes for fluorescence decay beginning at full excitation (lo) to progress down a first order decay waveform from full excitation to 1/e is less than 20 nanoseconds for known glucose indicators (note: to the best of my knowledge). In order to sufficiently characterize the waveform at such a fast interval by direct measurement according to the definition, it is necessary to sample the decaying amplitude following excitation at a much faster rate in order to get a sufficient number of data points to define the curve and determine 1/e in time. For example, just five data points along the curve would require sampling at 20/5=4 nanosecond sample intervals. This illustrates the preference/necessity for expensive, large, and complex phase modulation signal processing equipment and techniques in measuring nanosecond range fluorescent lifetimes which must be deconvoluted by complex algorithms. In one example of an advanced microcontroller based design for decay time measurement within a consumer or medical type device, the sampling rate of an analog to digital converter (ADC) block operating within a state of the art (201) integrated System on a Chip (SOC) microcontroller (Nordic nrf51 Series) with optical detection and input directly from a sensL 3 mm Silicon photomultiplier (SiPM) chip is limited to between 5 and 20 microseconds sampling rate in such a setup. It may not be possible to use this setup with nanosecond decay times. The fluorescent measurement requires much more speed and advanced methods using expensive equipment as represented by phase modulation, which although very well serving chemistry research measurement use, is not at all suited for consumer or most medical type applications.

EXAMPLES

Synthesis of the compositions described herein will be performed based on the following approaches.
Synthesis of Metalloporphyrin The synthesis of metalloporhyrins and various derivatives as described can be accomplished by multiple means known to those skilled in the art with some examples referenced as follows:

One-pot general synthesis of metalloporphyrins, is described in Anil Kumar, Suman Maji, Prashant Dubey, G. J. Abhilash, Sohini Pandey, Sabyasachi Sarkar,Tetrahedron Letters, Volume 48, Issue 41, 8 Oct. 2007, Pages 7287-7290; The Porphyrin Handbook: Synthesis and organic chemistry, Volume 1 By Karl M. Kadish, 2000, Academic Press, San Diego, Calif., which is incorporated herein by reference in its entirety. An example general synthesis for the metalloporphyrin is as follows:

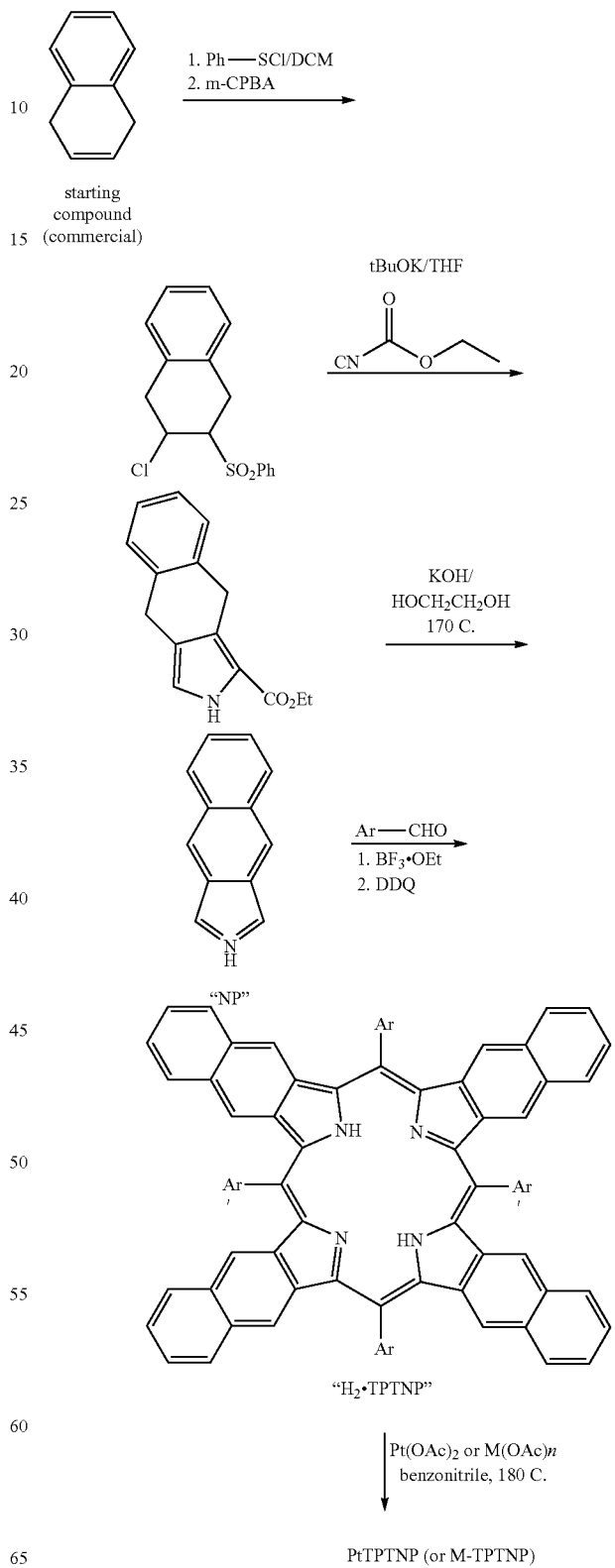

Addition of Boronate Recognition Element

There are also multiple known methods of adding or including the boronate recognition element within the structure. One example is a Miyaura Borylation Reaction:

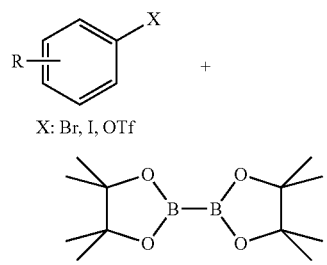

X: Br, I, OTf

Other reactions that can be used to incorporate boronate are also well known, such as described by Organic Chemistry Portal, Sysnthesis of arylboronic acids and arylboronates, http://www.organic-chemistry.org/synthesis/C1B/boronicacids/arylboronicacids.shtm (accessed Jun. 17, 2016), which is incorporated herein by reference in its entirety.

For example, the boronate may be introduced as the preferred napthyl pyrrole porphyrin precursor as a mono or bis B—N boronate (Example A):

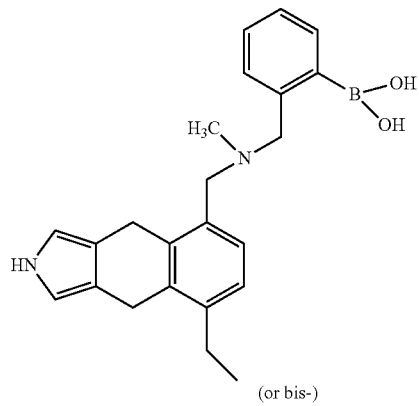 [SMILES: CCc1ccc(CN(C)Cc2ccccc2B(O)O)c2c1Cc1c[nH]cc1C2]

(or bis-)

Or as a simple monoboronate only (Example B):

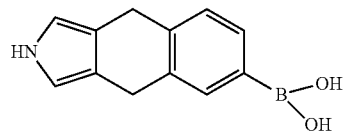 [SMILES: OB(O)c1ccc2c(c1)Cc1c[nH]cc1C2]

Where Example A would result in a synthesis as shown:

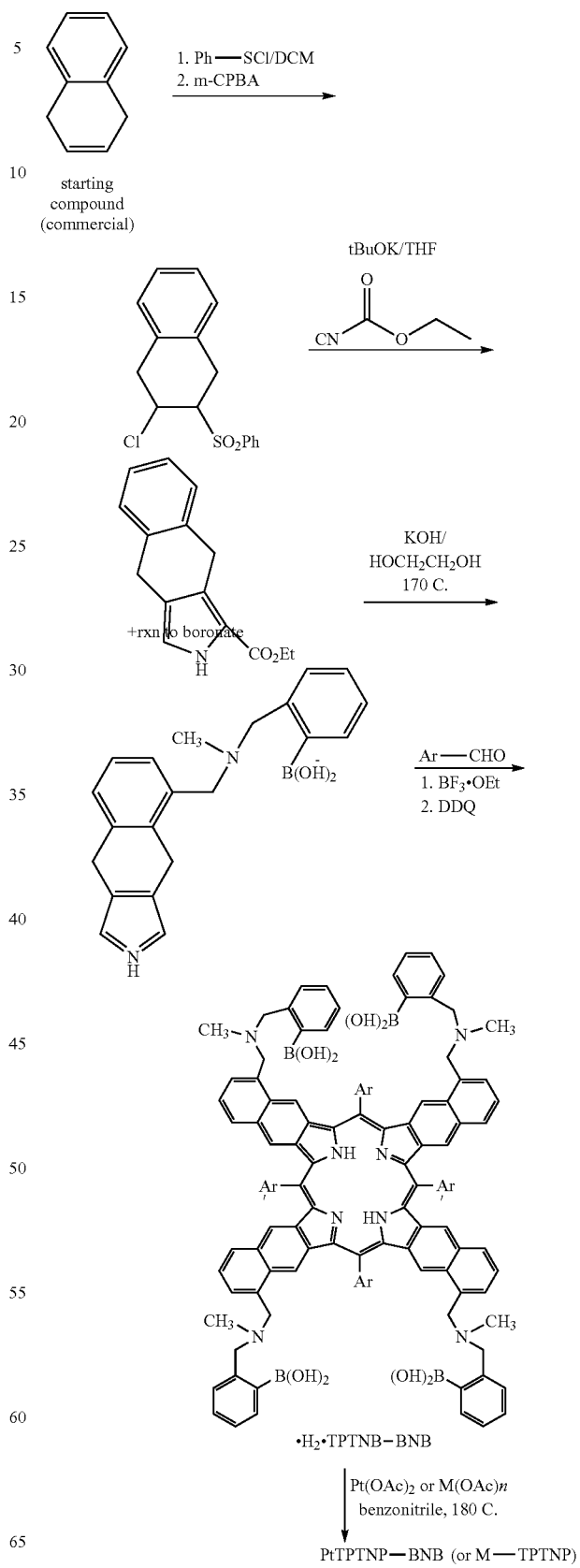

•H₂•TPTNB—BNB

PtTPTNP—BNB (or M—TPTNP)

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed is:

1. A compound having the following structure:

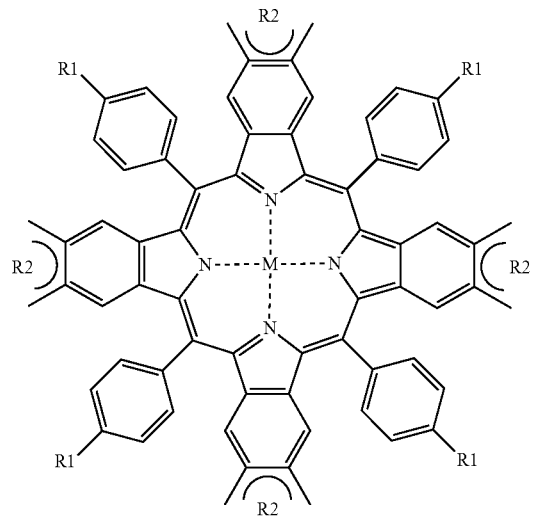

wherein M is a metal which forms a chelated luminescent complex with tetraphenyl porphyrin ligand base structure or derivatives thereof;
  each R1 is independently a linker group, a polymerizable group, or H;
  each R2 independently comprises a phenyl, napthyl, anthryl, wherein at least one R2 further comprises a recognition element capable of detecting an analyte, wherein the recognition element is a boronate or derivative thereof.

2. The compound of claim 1, wherein M is selected from the group consisting of: Pt, Pd, Al, Ru, Os, Ir, Al, Cu, Ag, Pb, Au, Eu, Tb, Rh, and Ni.

3. The compound of claim 1, wherein at least one R1 comprises:

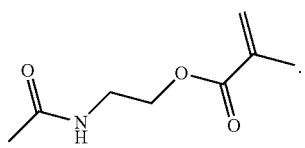

4. The compound of claim 1 wherein R1 is a linker group or H.

5. The compound of claim 1 wherein R1 is selected from the group consisting of: vinyl, acrylate, methacrylate, amides, polyethylene glycols, methacrylamides, carboxy, amine, sulfhydryl, and sulfonate.

6. The compound of claim 1, wherein R1 is selected from the group consisting of: vinyl, acrylate, methacrylate, amides, polyethylene glycols, and methacrylamides.

7. The compound of claim 1, wherein a polymeric backbone structure is covalently bonded to at least one R1.

8. The compound of claim 7, wherein the polymeric backbone structure is a polymer, a copolymer, a hydrogel, or a derivative thereof.

9. The compound of claim 1, wherein the at least one R2 further comprising a recognition element is selected from the group consisting of boronate coupled into a phenyl, napthyl, anthryl; a bis-boronate coupled into a phenyl, napthyl, anthryl; mono boronates of phenyl boronate, napthyl boronate, anthryl boronate; and bis-boronate derivations of phenyl, napthyl, or anthryl groups.

10. The compound of claim 1, wherein each R2 further comprising a recognition element is independently selected from the group consisting of:

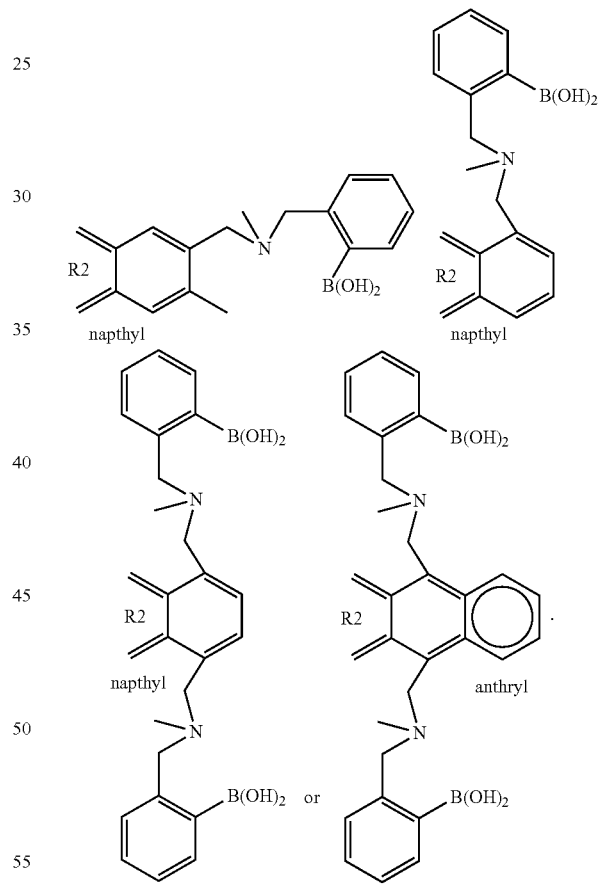

11. The compound of claim 1, wherein the analyte is glucose.

12. The compound of claim 1 wherein two R2s further comprise a recognition element.

13. The compound of claim 1 wherein three R2s further comprise a recognition element.

14. The compound of claim 1 wherein four R2s further comprise a recognition element.

15. The compound of claim 1 wherein at least one R2 does not comprise a recognition element.

16. The compound of claim 15 wherein the at least one R2 not comprising a recognition element is napthyl.

* * * * *